United States Patent
Rödjegård

(10) Patent No.: US 11,828,702 B2
(45) Date of Patent: Nov. 28, 2023

(54) METHOD AND DEVICE FOR DETERMINING A CONCENTRATION OF A COMPONENT IN A FLUID

(71) Applicant: Senseair AB, Delsbo (SE)

(72) Inventor: Henrik Rödjegård, Johanneshov (SE)

(73) Assignee: Senseair AB, Delsbo (SE)

( * ) Notice: Subject to any disclaimer, the term of this patent is extended or adjusted under 35 U.S.C. 154(b) by 0 days.

(21) Appl. No.: 18/251,530

(22) PCT Filed: Nov. 16, 2021

(86) PCT No.: PCT/SE2021/051148
§ 371 (c)(1),
(2) Date: May 2, 2023

(87) PCT Pub. No.: WO2022/108506
PCT Pub. Date: May 27, 2022

(65) Prior Publication Data
US 2023/0304924 A1    Sep. 28, 2023

(30) Foreign Application Priority Data
Nov. 18, 2020    (SE) .................................... 2051347-9

(51) Int. Cl.
*G01N 21/31* (2006.01)
*G01N 33/497* (2006.01)
(Continued)

(52) U.S. Cl.
CPC ........... *G01N 21/31* (2013.01); *G01N 21/274* (2013.01); *G01N 33/004* (2013.01); *G01N 33/497* (2013.01)

(58) Field of Classification Search
CPC ...... G01N 21/31; G01N 21/274; G01N 21/61; G01N 33/497; G01N 33/0006; G01N 33/004; G01N 33/4972; G01N 2033/4975
See application file for complete search history.

(56) References Cited

U.S. PATENT DOCUMENTS 9,846,117 B2    12/2017    Zhou et al.
2003/0109795 A1    6/2003    Webber
(Continued)

FOREIGN PATENT DOCUMENTS

WO    WO 2012166585 A2    12/2012
WO    WO 2016020422 A1    2/2016

OTHER PUBLICATIONS

Hodgkinson, J. and Tatam, RP., "Optical gas sensing: a Review", Topical Review, Measurement Science and Technology 24 012004 (2013). doi: 10.1088/0957-0233/24/1/012004; figure 15; Section 4.
(Continued)

*Primary Examiner* — Maurice C Smith
(74) *Attorney, Agent, or Firm* — Knobbe, Martens, Olson & Bear, LLP

(57) ABSTRACT

A method and a device for determining a concentration of a component in a fluid is described. The method comprises the steps of providing from a first optical sensor (1) a first light intensity (IR1A) for light which has interacted with the fluid at a first point in time (A), and a second light intensity (IR1B) for light which has interacted with the fluid at a second point in time (B), wherein the first light intensity (IR1A) is different from the second light intensity (IR1B), and providing from a second optical sensor (2) a third light intensity (IR2A) for light which has interacted with the fluid at the first point in time (A), and a fourth light intensity (IR2B) for light which has interacted with the fluid at the second point in time (B). The method also comprises determining the concentration of the component in the fluid, measured by the first optical sensor (1), at the first point in time (A) and/or at the second point in time (B), based on the first light intensity (IR1A), the second light intensity (IR1B), the third light intensity (IR2A), the fourth light intensity (IR2B), a first concentration function (func1), a second
(Continued)

concentration function (func2), and correlation information (Corr).

12 Claims, 2 Drawing Sheets

(51) Int. Cl.
    *G01N 21/27*     (2006.01)
    *G01N 33/00*     (2006.01)

(56) References Cited

U.S. PATENT DOCUMENTS

| | | |
|---|---|---|
| 2006/0047445 A1 | 3/2006 | Williams et al. |
| 2015/0373285 A1 | 12/2015 | Morris et al. |
| 2017/0254737 A1 | 9/2017 | Ke et al. |
| 2018/0095028 A1 | 4/2018 | Jourdainne |
| 2019/0072489 A1 | 3/2019 | Camargo et al. |

OTHER PUBLICATIONS

T. Wiezbicki and E. P. Ribeiro, "Sensor drift compensation using weighted neural networks," 2016 IEEE Conference on Evolving and Adaptive Intelligent Systems (EAIS), 2016, pp. 92-97, doi: 10.1109/EAIS.2016.7502497.; whole document.
International Search Report and Written Opinion of the International Searching Authority for PCT/SE2021/051148 dated Aug. 12, 2021 in 10 pages.

METHOD AND DEVICE FOR DETERMINING A CONCENTRATION OF A COMPONENT IN A FLUID

TECHNICAL FIELD

The present invention relates to a method and a device for determining a concentration of a component in a fluid, which method compensates for measurement errors due to aging of a sensor used for the measurement of the component, and to a sensor device in which the method has been implemented.

BACKGROUND ART

The invention relates to maintenance-free sensors having a self-calibration function for compensating for measurement errors that occur over time, such as drift errors. The invention is applicable on any type of sensors but may specifically be suitable for gas sensors, and more specifically $CO_2$-sensors. Today, measurement errors can be handled in various ways as stated below:

The standard way of calibrating sensors today is the so-called ABC method (automatic baseline correction), where the background level is monitored by finding the minimum reading of the sensor. This is assumed to be 400 ppm and is used as a calibration point.

Some sensors use dual sources, where one source is activated very seldom and therefore assumed to be free from drift. That one is used for calibration of the other source. This method compensate for aging of the primary source.

Some sensors use dual detectors, where one detector measure a reference wavelength outside the IR-active region of the target gas. The reference signal is used to normalize the light intensity to compensate for light intensity drift.

Other sensors use dual detectors with identical filters on the two detectors and different path lengths, where the closest detector measures the light intensity and can be used for normalization. The effective path length will then be the difference between the two detectors. Such a sensor is described in WO 2012166585 A2.

Another known solution is scanning filters such as tuneable Fabry Perot-filters that can be scanned between a reference wavelength and the measurement wavelength can work according to the same principle as 3. (https://www.vaisala.com/en/vaisala-carbocapr-technology-demanding-environments).

Another solution is to use pressure modulation for drift compensation.

SUMMARY OF THE INVENTION

An object of the present invention is to provide a method and an optical sensor arrangement for determining a concentration of a component in a fluid, which takes into account the drift errors of the optical sensor arrangement, wherein the drift errors are taken into account in an alternative way to the methods and the devices of the prior art.

The object above is fulfilled with a method and a device according to the independent claims.

Further advantages are provided with the features of the dependent claims.

According to a first aspect of the invention a method is provided for determining a concentration of a component in a fluid. The method comprising the steps of providing from a first optical sensor, configured to measure an intensity of light which has interacted with the fluid, a first light intensity for light which has interacted with the fluid at a first point in time, and a second light intensity for light which has interacted with the fluid at a second point in time, wherein the first light intensity is different from the second light intensity. The method also comprises the step of providing from a second optical sensor, configured to measure an intensity of light which has interacted with the fluid, a third light intensity for light which has interacted with the fluid at the first point in time, and a fourth light intensity for light which has interacted with the fluid at the second point in time. The method also comprises the step of providing a first concentration function defining the concentration of a component in the fluid as a function of the light intensity from the first optical sensor. The method also comprises the step of providing a second concentration function defining the concentration of a component in the fluid as a function of the light intensity from the second optical sensor, wherein the first concentration function has a different dependency on the light intensity than the second concentration function. The method also comprises the steps of providing correlation information defining the correlation between the first concentration function and the second concentration function, and determining the concentration of the component in the fluid, measured by the first optical sensor, at the first point in time and/or at the second point in time, based on the first light intensity, the second light intensity, the third light intensity, the fourth light intensity, the first concentration function, the second concentration function, and the correlation information.

With the method according to the first aspect, the advantage is provided that compensation for drift may be achieved only by measuring at two different concentrations of the component at two different points in time.

The method relies on measurements at different times and different unknown concentrations of the component for derivation of the concentration of the component. In contrast, prior art methods may have different concentration functions but measure at only one point in time.

With the method, maintenance is eliminated as long as the gas concentration in the environment varies.

The time difference between the first point in time and the second point in time depends on the speed of change of the concentration of the component. If the speed of change is fast, the time difference may be on the order of seconds. If the speed of change is slow, the time difference may be on the order of hours or days. The most important factor is that the first light intensity is different from the second light intensity. However, the time difference should be sufficiently short such that the drift of the optical sensor arrangement does not affect the light intensity. The drift of the optical sensor arrangement typically has an effect on the light intensity on a timescale of weeks or months.

The feature that the first concentration function has a different dependency on the light intensity than the second concentration function means that a change in the concentration of the component will result in that the ratio between the first light intensity and the second light intensity, is different from the ratio between the third light intensity and the fourth light intensity.

The feature of providing correlation information defining the correlation between the first concentration function and the second concentration function means that the relationship between them is known.

The first optical sensor and the second optical sensor may be configured to measure the concentration of the same component. In this case, the correlation information defines that the first concentration function provides the same concentration as the second concentration function.

If the first optical sensor and the second optical sensor are configured to measure the concentration of different components, the correlation is a function describing their relationship. An example of this is an arrangement configured to measure ethanol and carbon dioxide in the breath from a person. The concentration of ethanol close to the mouth depends on the concentration of ethanol in the blood of the person. At a distance from the mouth the concentration of carbon dioxide and ethanol have decreased with the same factor. Thus, the concentration of carbon dioxide may be expressed as $$C\text{meas}CO_2 = C\text{background} + kC\text{measEtOH, wherein}$$

k in this case is an unknown constant, depending on the intoxication level of the person under test. In this case "k" can be obtained by including data from more concentrations during the breath. k is constant during the test since the intoxication remains constant.

The step of determining the concentration of the component in the fluid, measured by the first optical sensor, may comprise the steps of determining a first zero signal from the first optical sensor without any component present in the fluid, and/or a second zero signal from the second optical sensor without any component present in the fluid, wherein the first concentration function is a function also of the first zero signal and the second concentration function is a function also of the second zero signal.

It might be advantageous to determine the first zero signal and the second zero signal when determining the concentration of the component in the fluid, but depending on how the determination is performed it is not always necessary to determine the first zero signal and the second zero signal as part results.

Pairs of a light intensity from the first optical sensor and a light intensity from the second optical sensor may be provided at a plurality of points in time, wherein the first point in time and the second point in time are chosen such that the first sensor signal is different from the second sensor signal. The continuous provision of such pairs of light intensities facilitates the provision of light intensities. The light intensities may be stored in computer file and be retrieved when necessary.

According to a second aspect of the present invention, an optical sensor arrangement is provided for determining a concentration of a component in a fluid. The optical sensor arrangement comprises a first optical sensor configured to measure a light intensity for light, which has interacted with the fluid, wherein the concentration of a component in the fluid is defined by a first concentration function being a function of the light intensity from the first optical sensor. The optical sensor arrangement also comprises a second optical sensor configured to measure a light intensity for light which has interacted with the fluid, wherein the concentration of a component in the fluid is defined by a second concentration function being a function of the light intensity from the second optical sensor, wherein the first concentration function has a different dependency of the light intensity than the second concentration function. The optical sensor arrangement is characterized in that it is configured to measure with the first optical sensor, a first light intensity for light which has interacted with the fluid at a first point in time, and a second light intensity for light which has interacted with the fluid at a second point in time, wherein the first light intensity is different from the second light intensity. The optical sensor arrangement is configured to measure, with the second optical sensor, a third light intensity for light which has interacted with the fluid at the first point in time, and a fourth light intensity for light which has interacted with the fluid at the second point in time, determining the concentration of the component in the fluid, measured by the first optical sensor, at the first point in time and/or at the second point in time, based on the first light intensity, the second light intensity, the third light intensity, the fourth light intensity, the first concentration function, the second concentration function, and correlation information defining the correlation between the first concentration function and the second concentration function.

With the optical sensor arrangement according to the second aspect the advantage is provided that compensation for drift may be achieved only by measuring at two different concentrations of the component at two different points in time.

The invention relies on measurements at different times and different unknown concentrations of the component for derivation of the concentration of the component. In contrast, prior art devices may have different concentration functions but measure at only one point in time.

With the optical sensor according to the second aspect, maintenance is eliminated as long as the gas concentration in the environment varies.

The optical sensor arrangement has knowledge of the first concentration function and the first concentration function so that the concentration of the component may be determined.

The optical sensor arrangement may be arranged such that the time difference between the first point in time and the second point in time depends on the speed of change of the concentration of the component. If the speed of change is fast, the time difference may be on the order of seconds. If the speed of change is slow the time difference may be on the order of hours or days. The most important factor is that the first light intensity is different from the second light intensity. However, the time difference should be sufficiently short such that the drift of the optical sensor arrangement does not effect to light intensity. The drift typically has an effect on a timescale of weeks or months.

The feature that the first concentration function has a different dependency on the light intensity than the second concentration function means that a change in the concentration of the component will result in that the ratio between the first light intensity and the second light intensity, is different from the ratio between the third light intensity and the fourth light intensity.

The feature of providing correlation information defining the correlation between the first concentration function and the second concentration function means that the relationship between them is known.

The first optical sensor and the second optical sensor may be configured to measure the concentration of the same component. In this case, the correlation information defines that the first concentration function provides the same concentration as the second concentration function.

If the first optical sensor and the second optical sensor are configured to measure the concentration of different components the correlation is a function describing their relationship as explained and exemplified above in relation to the first aspect of the invention described.

The optical sensor arrangement may be configured to determine the concentration of the component in the fluid, measured by the first optical sensor, by determining a first zero signal from the first optical sensor without any component present in the fluid, and/or a second zero signal from the second optical sensor without any component present in the fluid, wherein the first concentration function is a function also of the first zero signal and the second concentration function is a function also of the second zero signal.

The optical sensor arrangement may be configured to measure pairs of a light intensity from the first optical sensor and a light intensity from the second optical sensor at a plurality of points in time, and wherein the first point in time and the second point in time are chosen such that the first sensor signal is different from the second sensor signal. This provides the same advantages as has been described above in relation to the first aspect of the invention.

The first optical sensor may comprise a fluid cavity and a first light detector configured to measure an intensity of the light, which has interacted with the fluid in the fluid cavity. The second optical sensor may comprise a second light detector configured to measure an intensity of the light, which has interacted with the fluid in the fluid cavity. By having such a fluid cavity, the absorption length in the fluid is well defined. A difference between the first concentration function and the second concentration function may be obtained by varying the cross section of the fluid cavity.

The first optical sensor and the second optical sensor may be configured to measure the light intensity in the same wavelength band. This is preferable if the first optical sensor and the second optical sensor are to measure the same component in the fluid.

The optical sensor arrangement may comprise a first band pass filter in front of the first light detector and a second band pass filter in front of the second light detector. Band pass filters in front of the light detectors is a simple way of providing filtration in a wavelength band. Another way of providing wavelength filtration is to use a light source, which emits light in the desired wavelength range.

Interesting wavelengths for detection are in the wavelength range 1-10 μm, and preferably in the wavelength range 2-6 μm.

The optical sensor may be configured such that the light to the first light detector travels a longer distance through the fluid than the light to the second light detector. Alternatively or additionally, the filters may have different light filtering properties.

The optical sensor arrangement may comprise a first light source emitting light to interact with the fluid in the fluid cavity and a second light source emitting light to interact with the fluid in the fluid cavity, wherein the first light detector is configured to measure the intensity of light from the first light source, and wherein the second light detector is configured to measure the intensity of light from the second light source. With the sensors arranged in this way it is possible to have the optical sensors separated from each other.

It is possible to configure the optical sensor arrangement with two light sources and one light detector. According to one option, the wavelength filtration may be performed at the light source side with different wavelength bands for each detector, with the single detector detecting both wavelength bands. According to another option the wavelength filtration may be performed anywhere while the single detector detects light form both light sources. In both options, the first light source may be pulsed with a first frequency and the second light source may be pulsed with a second frequency. The detector separates the different detected signals by electronic separation of the detected signals.

In the following description of embodiments of the invention, reference will be made to the appended drawings.

DETAILED DESCRIPTION

Figure 1:
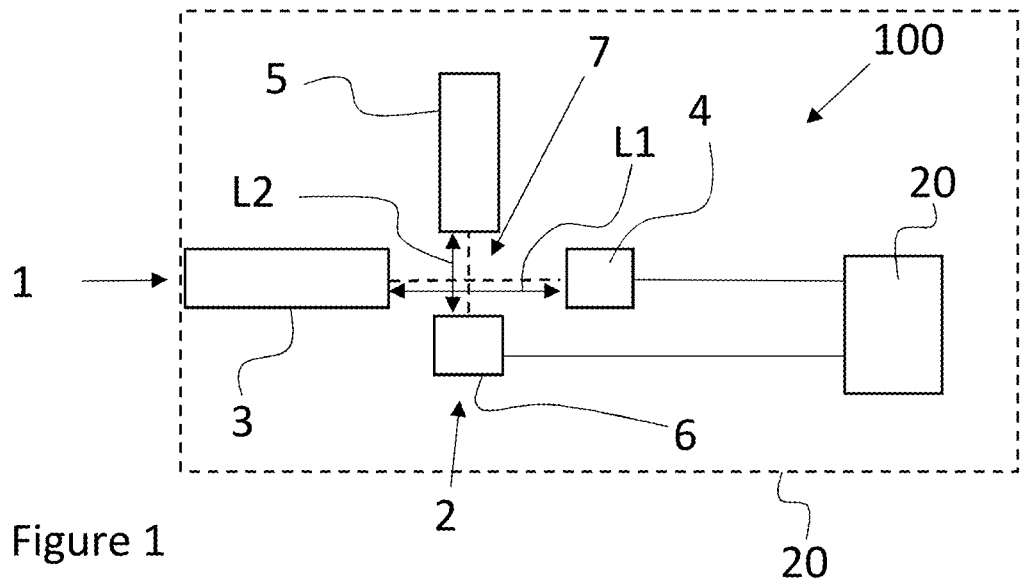
FIG. 1 shows an optical sensor arrangement according to an embodiment of the invention.

In the following description of embodiments of the invention, reference will be made to the appended drawings. The same reference numerals will be used for similar features in the different drawings.

FIG. 1 shows an optical sensor arrangement 100 for determining a concentration of a component in a fluid. The optical sensor arrangement 100 comprises a first optical sensor 1, which comprises a first light source 3, a first light detector 4, a second light source 5 and a second light detector 6. The optical sensor arrangement 100 also comprises a fluid cavity 7, which is arranged to carry the fluid. In the embodiment of FIG. 1, the fluid cavity 7 is shown as a space into which the fluid enters. The first light source 3 is configured to emit light into the fluid cavity to interact with the fluid in the fluid cavity 7 and towards the first light detector 4. The second light source 5 is configured to emit light into the fluid cavity 7 to interact with the fluid in the fluid cavity 7, and towards the second light detector 5. The first light source 3 is configured to emit light at a wavelength that corresponds to an absorption peak of the component to be detected in the fluid. In the described embodiment, the second light source 5 is configured to emit light at the same wavelength as the first light source 3. The first light detector 4, and thereby also the first optical sensor 1, is configured to measure the intensity of light from the first light source 3. The second light detector 6, and thereby also the second optical sensor 2 is configured to measure the intensity of light from the second light source 5. The width of the fluid cavity 7 defines a first absorption path length L1 for the light from the first light source 3 to the first light detector 4. The height of the fluid cavity 7 defines a second absorption path length L2 for the light from the second light source 5 to the second light detector 6. The first absorption length L1 is larger than the second absorption length. The first light source 3 and the second light source 5 are in this embodiment configured to emit light at the same wavelength, which is adapted to an absorption peak of the component to be detected. The first light detector 4 and the second light detector 6 are arranged to detect light, which has interacted with the fluid in the fluid cavity. The first zero signal, i.e., the light intensity detected by the first light detector 4 without any component present in the fluid, is denoted I01. The second zero signal, i.e., the light intensity detected by the second light detector 6 without any component present in the fluid, is denoted I02. The first light detector 4 and the second light detector 6 are both connected to a control unit 20, which is configured for analysation of the detected signals. The control unit 20 may be implemented as, e.g., a computer or an FPGA. The dashed line 21 illustrates that the first optical sensor 1 the second optical sensor 2, and the control unit 20 may be integrated within a common cover.

When a component is present in the fluid, some of the light from the first light source 3 and the second light source 5 will be absorbed by the component in the fluid. The part of the light that is absorbed in the fluid is dependent on the absorption path length and the concentration of the component in the fluid. The light intensity IR1 detected by the first light detector 4 is a function of the concentration of the component Cmeas1 and the first zero signal I01. The light intensity detected by the second light detector 6 is a function of the concentration of the component and the second zero signal I02. Alternatively, the concentration of the component Cmeas1 may be expressed as a function of the light intensity detected by the first light detector 4 as Cmeas1=func1(IR1, I01), wherein func1(IR1, I01) is a function which has been determined in advance. Correspondingly, the concentration of the component measured by the second optical sensor 2 may be expressed as Cmeas2=func2(IR2, I02), wherein func2(IR2, I02) is a function which has been determined in advance. Due to the different absorption path lengths L1, L2, the first concentration function (func1) has a different dependency of the light intensity than the second concentration function (func2).

The optical sensor arrangement 100 is configured to measure, with the first optical sensor 1, a first light intensity IR1A for light which has interacted with the fluid at a first point in time A, and a second light intensity IR1B for light, which has interacted with the fluid at a second point in time B. The first light intensity IR1A is different from the second light intensity IR1B. The optical sensor arrangement 100 is configured to measure, with the second optical sensor 2, a third light intensity IR2A for light which has interacted with the fluid at the first point in time A, and a fourth light intensity IR2B for light which has interacted with the fluid at the second point in time B. The third light intensity IR2A will be different from the fourth light intensity IR2B.

The different light intensities may be achieved in many different ways. The optical arrangement 100 may be configured to measure pairs of a light intensity IR1 from the first optical sensor 1 and a light intensity IR2 from the second optical sensor 2 at a plurality of points in time. The first point in time and the second point in time are chosen such that the first sensor signal IR1A is different from the second sensor signal IR1B. The pairs of a light intensity IR1 from the first optical sensor 1 and a light intensity IR2 from the second optical sensor 2 may be stored in a memory in chronological order.

The concentration of the component in the fluid, measured by the first optical sensor 1, at the first point in time A and/or at the second point in time B, may then be determined based on the first light intensity IR1A, the second light intensity IR1B, the third light intensity IR2A, the fourth light intensity IR2B, the first concentration function func1, the second concentration function func2, and correlation information Corr defining the correlation between the first concentration function func1 and the second concentration function func2.

The determination may be performed according to the following description.

The concentration $Cmeas1_A$ measured with the first optical sensor 1 at the first point in time A has to be equal to the concentration $Cmeas2_A$ measured with the second optical sensor 2 at the first point in time A as they measure on the same fluid, i.e., $Cmeas1_A=Cmeas2_A$. Also, the concentration $Cmeas1_B$ measured with the first optical sensor 1 at the second point in time B has to be equal to the concentration $Cmeas2_B$ measured with the second optical sensor 2 at the second point in time A. As long as the first point in time is not too far from the second point in time the first zero signal I01 will not change and the second zero signal I02 will not change. The time difference between the first point in time and the second point in time is typically less than a day. With the knowledge that Cmeas1=func1(IR1, I01) and Cmeas2=func2(IR2, I02) we get the following equations:

$$Cmeas1_A = Cmeas2_A, \text{ i.e.,}$$

$$func1(IR1_A, I01_A) = func2(IR2_A, I02_A)$$

$$Cmeas1_B = Cmeas2_B, \text{ i.e.,}$$

$$func1(IR1_B, I01_B) = func2(IR2_B, I02_B)$$

$$I01_A = I01_B$$

$$I02_A = I02_B$$

The equation system above is possible to solve only if $Cmeas1_A$ is different from $Cmeas1_B$ and if func1 has a different dependency on IR1 than func2 on IR2. The latter requirement may be expressed as that the relative derivative of the IR signal is different between the two sensors in the concentration region A to B. We can rewrite the function func1 as IR1=funcinv (Cmeas1, I0), where Cmeas1 is the concentration of the component measured with the first optical sensor. The derivative [dIR/dC]/IR must be different for the first optical sensor 1 and the second optical sensor 2, i.e., the first optical sensor 1 and the second optical sensor 2 should absorb a different fraction of the light when going from concentration A to concentration B.

A larger difference between $Cmeas1_A$ and $Cmeas1_B$ will result in less sensitivity to measurement errors such as sensor noise and hence more accurate estimate of I01 and I02 as well as Cmeas1 and Cmeas1.

The equation system above can be solved and we can get a unique solution finding the values of Cmeas as well as I0. The derived I0 can be used for compensation of long-term drift by updating the calibration parameters in the sensors.

Numerical methods implemented in a computer or microcontroller can be used to update the I0. This can be done using single events, or incrementally, or by iteration.

As an example we can assume that the relation between concentration and IR-signal is described by the Beer-Lambert relation.

$$IR1 = I01 \cdot e^{-Cmeas1 \cdot Sens1}, \text{ and}$$

$$IR2 = I02 \cdot e^{-Cmeas2 \cdot Sens2}.$$

As an example we can assume the following. From factory calibration we know that Sens1=0.001[ppm−1] and Sens2=0.0005[ppm−1]. Hence, they have a difference in relative sensitivity, i.e., the derivative [dIR1/dC]/IR1 is different from [dIR2/dC]/dIR2.

At time A we know that the signal of the two sensors are $IR1_A=0.9836$ and $IR2_A=0.7288$. We also know that they are exposed to the same concentration of the target gas. At time B the gas concentration has changed, and we have $IR1_B=0.7412$ and $IR2_B=0.6326$. We may assume that the first zero signal I01 and the second zero signal I02 have not changed between the two occasions since the drift is slow. We also know that the two sensors are exposed to the same gas concentration. The equation system then becomes:

$$CA = -\ln(IR1_A/I01)/Sens1 = -\ln(0.9836/I01)/0.001$$

$$CA = -\ln(IR2_A/I02)/Sens2 = -\ln(0.7288/I02)/0.0005$$

$$CB = -\ln(IR1_B/I01)/Sens1 = -\ln(0.7412/I01)/0.001$$

$$CB = -\ln(IR2_B/I02)/Sens2 = -\ln(0.6326/I02)/0.0005$$

If the two uppermost and the two lowermost equations are put equal the result is:

$$-\ln(0.9836/I01)/0.001 = -\ln(0.7288/I02)/0.0005$$

$$-\ln(0.7412/I01)/0.001 = -\ln(0.6326/I02)/0.0005$$

The equation system can be solved, and we get the unknown first zero signal I01 and the unknown second zero signal I02 as:

$I01 = 1.5$ $I02 = 0.9$

The sensors can update the first zero signal I01 and the second zero signal I02 and hence compensate for the drift.

The first zero signal I01 and the second zero signal I02 can also be used to calculate the concentrations CA and CB as:

$Cmeas1_A = -\ln(IR1_A/I01)/Sens1 = -\ln(0.9836/1.5)/0.001 = 422$ ppm $Cmeas2_A = -\ln(IR2_A/I02)/Sens2 = -\ln(0.7288/0.9)/0.0005 = 422$ ppm $Cmeas1_B = -\ln(IR1_B/I01)/Sens1 = -\ln(0.7412/I01)/0.001 = 705$ ppm $Cmeas2_B = -\ln(IR2_B/I02)/Sens2 = -\ln(0.6326/I02)/0.0005 = 705$ ppm In reality the function is more complex than Beer-Lambert, but still known and unique. Numerical methods are used to solve the equation system.

The optical sensor arrangement 100 in the example above is configured to determine the concentration of the component in the fluid, measured by the first optical sensor 1, by determining a first zero signal I01 from the first optical sensor 1 without any component present in the fluid, and/or a second zero signal I02 from the second optical sensor 2 without any component present in the fluid. It is however possible to not determine the first zero signal I01 and the second zero signal I02, separately but to integrate this in the calculation of the concentrations Cmeas1 and Cmeas2.

The optical sensor arrangement 100 may be configured to measure pairs of a light intensity $IR1_A$ from the first optical sensor 1 and a light intensity $IR2_A$ from the second optical sensor 2 at a plurality of points in time, and wherein the first point in time and the second point in time are chosen such that the first sensor signal $IR1_A$ is different from the second sensor signal $IR1_B$.

Figure 2:
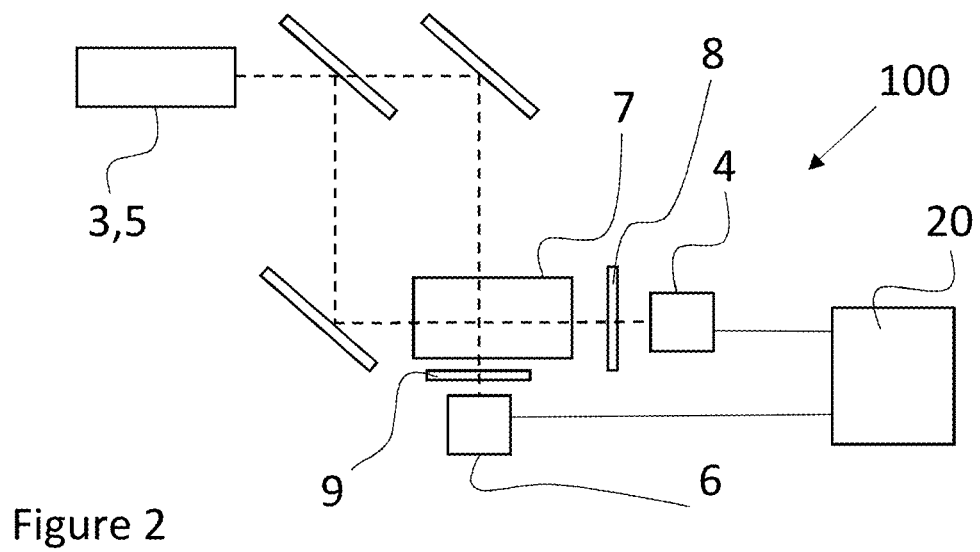
FIG. 2 shows an optical sensor arrangement according to an alternative embodiment of the invention.

In the optical sensor arrangement 100 as described in FIG. 2, the first optical sensor 1 and the second optical sensor 2 are configured to measure the light intensity in the same wavelength band as the component that is measured is the same in the first optical sensor 1 as well as the second optical sensor 2. Thus, the first band pass filter 8 is the same as the second band pass filter 9.

It is also possible to measure concentrations of different gases with the first optical sensor 1 and the second optical sensor 2, if the concentrations of the two components have a known relationship, i.e., if the first component is correlated with the second component. The first optical sensor 1 is configured to measure a component X and the first band pass filter 8 is adapted to an absorption wavelength of component X. The second optical sensor 2 is configured to measure a component Y and the second band pass filter 9 is adapted to an absorption wavelength of component Y. For instance, when analysing a breath there is a known correlation between $CO_2$ and humidity, i.e., $H_2O$, that can be used for self-calibration. In this case we have a correlation function "Corr" describing the relation between $CO_2$ (component X) and $H_2O$ (component Y), so that:

$Cmeas1 = Corr(Cmeas2) = Corr(CmeasY(IR2, I02))$

The four measurements of two different gases at two different occasions can in that case be described as:

$Cmeas1_A(IR1_A, I01_A)$ $Cmeas1_B(IR1_B, I01_B)$ $Cmeasas2_A(IR2_A, I02_A)$ $Cmeas2_B(IR2_B, I02_B)$ And the resulting equation system then becomes:

$Cmeas1_A(IR1_A, I01_A) = Corr(Cmeasas2_A(IR2_A, I02_A)$ $Cmeas1_B(IR1_B, I01_B) = Corr(Cmeas2_B(IR2_B, I02_B))$ $I01_A = I01_B$ $I02_A = I02_B$ The equation can be solved if the correlation function Corr is known. The correlation function Corr, can either be known from calibration or physical correlation. It can also be obtained from self-characterization, where more data points at different concentrations are added.

The first zero signal I01 and the second zero signal I02 may be used to re-calibrate the first optical sensor 1 and the second optical sensor 2. In this way the drift of the first zero signal I01 and the second zero signal I02 may be compensated for. The determination of the first zero signal I01 and the second zero signal I02 may be made at regular intervals such as, e.g., once a day.

In a breathalyser, where ethanol vapour and CO2 is sensed one knows the correlation between the two gases. The first optical sensor 1 measures the concentration of carbon dioxide $CO_2$ and the second optical sensor 2 measures the concentration of ethanol. We can write Cmeas1 as $CmeasCO_2$ and the Cmeas1 as CmeasEtOH. This gives $CmeasCO_2 = Corr(CmeasEtOH) = Cbackground + kCmeasEtOH$, wherein k in this case is an unknown constant, depending on the intoxication level of the person under test. In this case "k" can be obtained by including data from more concentrations during the breath. The unknown constant k is constant during the test since the intoxication remains constant.

Figure 3:
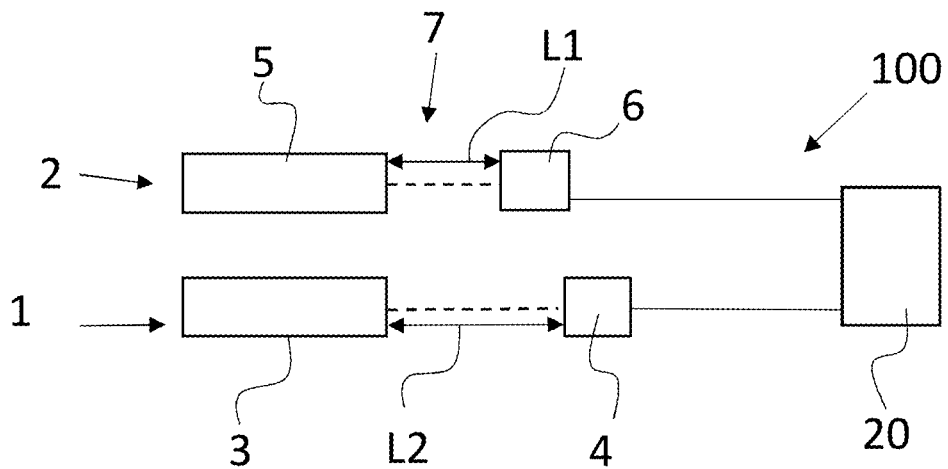
FIG. 3 shows an optical sensor arrangement according to an alternative embodiment of the invention.
Figure 4:
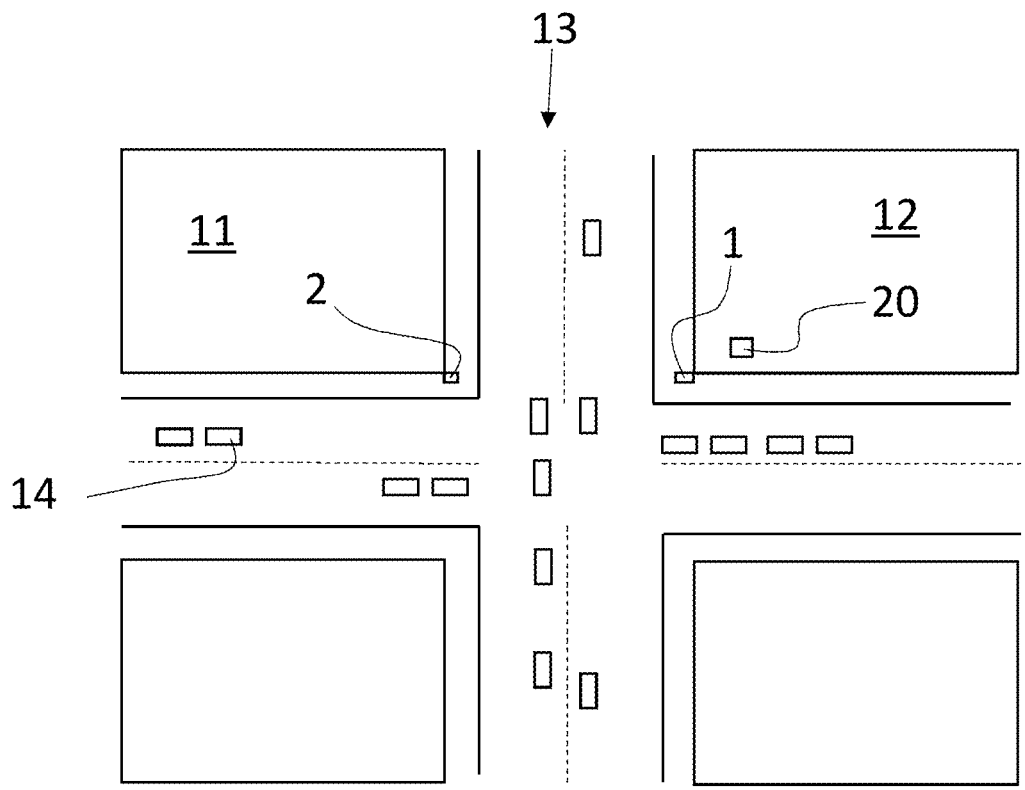
FIG. 4 shows an optical sensor arrangement according to an alternative embodiment arranged at a street crossing.

FIG. 3 shows schematically an optical sensor arrangement 100 comprising a first optical sensor 1 and a second optical sensor 2 and a control unit 20. The only difference between the optical sensor arrangement 100 in FIG. 3 and the optical sensor arrangement 100 in FIG. 1 is that the first optical sensor and the second optical sensor are arranged side by side in FIG. 3. As is illustrated by the dashed lines FIG. 4 shows schematically an optical sensor arrangement 100 comprising a first optical sensor 1 and a second optical sensor 2 and a control unit 20 arranged in a street crossing 13. The first optical sensor 1 and the second optical sensor 2 may be as shown in FIG. 3, with the difference that they are separated with a larger distance in FIG. 4. The control unit is configured to communicate wirelessly with the first optical sensor 1 and the second optical sensor 2. The first optical sensor 1 is arranged on the corner of a first building 11 while the second optical sensor 2 is arranged on the corner of a second building 12. A plurality of cars 14. The cars 14 emit carbon dioxide, which is monitored by the optical sensor arrangement. The first optical sensor 1 and the second optical sensor 2 are configured to measure on the same absorption wavelength of carbon dioxide. Usually the traffic is lower during the night than during the day, which will result in a varying concentration of carbon dioxide at the street crossing with a higher concentration of carbon dioxide during the day. The concentration of carbon dioxide evens out in the street crossing leading to essentially the same concentration at the first optical sensor 1 as the second optical sensor 2. The concentration is registered by both optical sensors 1, 2, continuously at regular intervals and sent to the control unit 20. By choosing the first point in time A to be during the day and the second point in time B to be during the night the concentration of carbon dioxide will differ making it possible to determine the first zero signal I01 and the second zero signal I02 and the measured concentrations $Cmeas1_A$, $Cmeas1_B$, $Cmeas2_A$, $Cmeas2_B$, using the method described above. In contrast to the embodiments shown in FIG. 1 and FIG. 2, the optical sensor arrangement 100 in the embodiment shown in FIG. 4 have the first optical sensor 1, the second optical sensor 2, and the control unit are separated from each other.

The above described embodiments may be amended in many ways without departing from the scope of the invention which is limited only by the appended claims.

The invention claimed is:

1. A method for determining a concentration of a component in a fluid, comprising:
    providing from a first optical sensor, configured to measure an intensity of light which has interacted with the fluid, a first light intensity for light which has interacted with the fluid at a first point in time, and a second light intensity for light which has interacted with the fluid at a second point in time, wherein the first light intensity is different from the second light intensity,
    providing from a second optical sensor, configured to measure an intensity of light which has interacted with the fluid, a third light intensity for light which has interacted with the fluid at the first point in time, and a fourth light intensity for light which has interacted with the fluid at the second point in time,
    providing a first concentration function defining the concentration of a component in the fluid as a function of the light intensity from the first optical sensor,
    providing a second concentration function defining the concentration of a component in the fluid as a function of the light intensity from the second optical sensor, wherein the first concentration function has a different dependency on the light intensity than the second concentration function,
    providing correlation information defining the correlation between the first concentration function and the second concentration function,
    determining the concentration of the component in the fluid, measured by the first optical sensor, at the first point in time and/or at the second point in time, based on the first light intensity, the second light intensity, the third light intensity, the fourth light intensity, the first concentration function, the second concentration function, and the correlation information.

2. The method according to claim 1, wherein the first optical sensor and the second optical sensor are configured to measure the concentration of the same component, and wherein the correlation information defines that the first concentration function provides the same concentration as the second concentration function.

3. The method according to claim 1, wherein the step of determining the concentration of the component in the fluid, measured by the first optical sensor, comprises the steps of determining a first zero signal from the first optical sensor without any component present in the fluid, and/or a second zero signal from the second optical sensor without any component present in the fluid, wherein the first concentration function is a function also of the first zero signal and the second concentration function is a function also of the second zero signal.

4. The method according to claim 1, wherein pairs of a light intensity from the first optical sensor and a light intensity from the second optical sensor are provided at a plurality of points in time, and wherein the first point in time and the second point in time are chosen such that the first sensor signal is different from the second sensor signal.

5. An optical sensor arrangement for determining a concentration of a component in a fluid, comprising:
    a first optical sensor configured to measure a light intensity for light which has interacted with the fluid, wherein the concentration of a component in the fluid is defined by a first concentration function being a function of the light intensity from the first optical sensor,
    a second optical sensor configured to measure a light intensity for light which has interacted with the fluid, wherein the concentration of a component in the fluid is defined by a second concentration function being a function of the light intensity from the second optical sensor, wherein the first concentration function has a different dependency of the light intensity than the second concentration function,
    wherein the optical sensor arrangement is configured to measure, with the first optical sensor, a first light intensity for light which has interacted with the fluid at a first point in time, and a second light intensity for light which has interacted with the fluid at a second point in time, wherein the first light intensity is different from the second light intensity, wherein the optical sensor arrangement is configured to measure, with the second optical sensor, a third light intensity for light which has interacted with the fluid at the first point in time, and a fourth light intensity for light which has interacted with the fluid at the second point in time,
    determining the concentration of the component in the fluid, measured by the first optical sensor, at the first point in time and/or at the second point in time, based on the first light intensity, the second light intensity, the third light intensity, the fourth light intensity, the first concentration function, the second concentration function, and correlation information defining the correlation between the first concentration function and the second concentration function.

6. The optical sensor arrangement according to claim 5, configured to determine the concentration of the component in the fluid, measured by the first optical sensor, by determining a first zero signal from the first optical sensor without any component present in the fluid, and/or a second zero signal from the second optical sensor without any component present in the fluid, wherein the first concentration function is a function also of the first zero signal and the second concentration function is a function also of the second zero signal.

7. The optical sensor arrangement according to claim 5, configured to measure pairs of a light intensity from the first optical sensor and a light intensity from the second optical sensor at a plurality of points in time, and wherein the first point in time and the second point in time are chosen such that the first sensor signal is different from the second sensor signal.

8. The optical sensor arrangement according to claim 5, wherein the first optical sensor comprises a fluid cavity, and a first light detector configured to measure an intensity of the light, which has interacted with the fluid in the fluid cavity, and wherein the second optical sensor comprises and a second light detector configured to measure an intensity of the light, which has interacted with the fluid in the fluid cavity.

9. The optical sensor arrangement according to claim 8, wherein the first optical sensor and the second optical sensor are configured to measure the light intensity in the same wavelength band.

10. The optical sensor arrangement according to claim 9, comprising a first band pass filter in front of the first light detector and a second band pass filter in front of the second light detector.

11. The optical sensor according to claim 6, wherein the light to the first light detector travels a longer distance through the fluid than the light to the second light detector.

12. The optical sensor according to claim 6, comprising a first light source emitting light to interact with the fluid in the fluid cavity and a second light source emitting light to interact with the fluid in the fluid cavity, wherein the first light detector is configured to measure the intensity of light from the first light source, and wherein the second light detector is configured to measure the intensity of light from the second light source.

* * * * *